United States Patent [19]

Avron et al.

[11] Plant 4,511

[45] Mar. 18, 1980

[54] ALGA STRAIN

[75] Inventors: Mordhay Avron, Rehovot; Ami Ben-Amotz, Ramat Gan, both of Israel

[73] Assignee: Yeda Research & Development Co. Ltd., Rehovot, Israel

[21] Appl. No.: 955,007

[22] Filed: Oct. 20, 1978

Related U.S. Application Data

[63] Continuation-in-part of Ser. No. 918,802, Jun. 26, 1978.

[51] Int. Cl.[2] ..... A01H 13/00

[52] U.S. Cl. ..... Plt./89

[58] Field of Search ..... Plt./89

*Primary Examiner*—Robert E. Bagwill

*Attorney, Agent, or Firm*—Browdy and Neimark

[57] ABSTRACT

An alga named *Dunaliella bardawil* is similar to *D. salina* except that its length is 15–19 μm, its diameter 10–14 μm and its volume 200–1000 μm³, and it contains large quantities of carotene and glycerol.

1 Drawing Figure

1

This application is a continuation-in-part of utility application, Ser. No. 918,802, filed June 26, 1978, the contents of which are hereby incorporated by reference.

The present invention relates to a new and distinct variety of alga known as *Dunaliella bardawil* (ATCC 30861). This new species, which has been isolated and cultivated as a pure algal culture, belongs to the Class of Chlorophycae, Order of Volvocales and has been deposited in the University of Texas International Culture Collection of Algae, Austin, Tex., 78712.

The algae of the present invention are unicellular motile cells of about 15 to 19 μm long and 10 to 14 μm in diameter, which are broadly ovoid or ellipsoid in shape with a fine elastic periplast but with no rigid cell wall. Two flagella 1.5 to 2 times the length of the cell emerge from one edge of the long cell axis, one large chloroplast occupies about half the cell volume and is often arranged in a cup-shape around the nucleus. A single median pyrenoid is embedded in the basal portion of the chloroplast and surrounded by starch granules. The cell volume is 200 to 1000 μm³. The cells reproduce vegetatively by longitudinal division of the motile cells.

For maximal β-carotene production the algae must be cultivated under an adequately high intensity of illumination, and this is best carried out outdoors in sunlight. If artificial light is used, the intensity of illumination ought to be at least about 1500 f.c. When cultivated outdoors the depth of the water ought not to exceed about 15 cm, and the optimum is about 5 cm.

In the following the content of glycerol, carotene, chlorophyll and protein of the algae are specified, both when grown outdoors, and under low intensity (200 f.c.) artificial illumination.

Content of β-carotene, Glycerol, Chlorophyll and Protein under favorable conditions:

| | Growth outdoors, 3 M NaCl | Growth indoors, 3 M NaCl |
|---|---|---|
| β-carotene pg/cell | 50–90 | 8–16 |
| Glycerol pg/cell | 300–400 | 200–275 |
| Chlorophyll pg/cell | 4–8 | 10–16 |
| Carotene mg/g dry wt. | 50–90 | 10–21 |
| Glycerol mg/g dry wt. | 300–400 | 270–370 |
| Chlorophyll mg/g dry wt. | 8–12 | 13–21 |

2

-continued

Content of β-carotene, Glycerol, Chlorophyll and Protein under favorable conditions:

| | Growth outdoors, 3 M NaCl | Growth indoors, 3 M NaCl |
|---|---|---|
| Protein mg/g dry wt. | 300–400 | 300–400 |

The cultivation is carried out either in an artificial medium or on seawater adjusted so as to contain the required nutrients and salt concentration.

An artificial medium ought to contain the following nutrients:

NaCl, 1–5 M, and preferably 3–4 M; $Mg^{++}$, 1–500 mM, and preferably 5 mM; $K^{+}$, 1–10 mM; $Ca^{++}$, 0.1–20 mM and preferably 0.2–0.4 mM, iron source, such as Fe-EDTA 0.5–45 μM, and preferably 1–2 μM; $SO_4^{--}$, 1–5 mM; Nitrogen source, as $NO_3^{-}$, 1–20 mM and preferably 3–4 mM, or $NH_4NO_3$, 0.5–2.5 mM and preferably 1–2 mM; phosphate, 0.01–1 mM.

It is possible to use seawater augmented by addition of various constituents or concentrated by partial evaporation and addition of certain constituents. This ought to have a sodium chloride content of up to 1–4.5 M NaCl and preferably 3 M NaCl supplemented with a nitrogen source such as $NH_4NO_3$, 0.5–2.5 mM, and preferably 1–2 mM, phosphate source such as $KH_2PO_4$, 0.01–1 mM, and preferably 0.1 mM, and an iron source such as $FeCl_3$-EDTA, 0.5–50 μM, preferably 2 μM.

There must be provided a suitable and adequate source of carbon such as 10 mM $NaHCO_3$ or $CO_2$ at about 300 liter $CO_2$ per m³ growth medium per day. When $CO_2$ is used as the carbon source, it is added by demand via a pH controlled solenoid valve. Other inorganic carbon sources such as $CaCO_3$, organic carbon sources such as sewage water, etc., are also suitable for growth.

The optimum pH for cultivation is between 7.0 and pH 9.0 and this is advantageously adjusted by adding required quantities of carbon dioxide, mineral acids such as hydrochloric acid or nitric acid, via a pH controlled valve.

The optimum temperature of cultivation is in the range of about 25°–35° C., and the algae withstand temperatures of about 4° C. to 40° C.

Various contaminant microorganisms, such as fungi, zooplankton, crustaceae etc. constitute a problem under conditions of large-scale cultivation and this can be overcome to a very large extent by carrying out the cultivation at a sodium chloride concentration of above about 3.0 M. The content of glycerol increases with the concentration of the sodium chloride in the growth medium. It is desirable to effect cultivation around 3.0 M NaCl.

In order to obtain a high content of carotene it is necessary to provide adequate intensity of illumination, as pointed out above. It is further helpful to supply a limiting concentration of nitrogen which can be provided in forms such as potassium nitrate, sodium nitrate, ammonium nitrate or by ammonia. When cultivation is carried out at a high sodium chloride content and under strong illumination, the nitrogen content ought to be below 4 mM; when cultivation is effected under lesser intensitites of illumination and at a smaller sodium chloride concentration, the nitrogen content ought not to exceed about 1 mM for optimum carotene content. A diurnal cycle ought to be maintained as under constant intense illumination severe inhibition of growth takes place.

The rate of reproduction of the algae is higher when the concentration of sodium chloride is not too high. The rate at about 1.5 M is about twice that at 4 M NaCl. In view of this it is possible to carry out a first step of cultivation at a lower sodium chloride concentration and to transfer the algae to a culture medium having a higher content of sodium chloride or to increase the NaCl content of the medium.

The algae are quite large and heavy, especially when the cultivation is terminated at a high sodium chloride content and in view of this it is easy to harvest the algae by sedimentation.

The glycerol and carotene can be recovered from the algae and there remains a residue having a high protein content. The amino acid composition of the algae and of the algae meal remaining after solvent extraction is as follows:

| | Amino Acids Analysis of Dunaliella bardawil | |
|---|---|---|
| Amino acid: | Dried algae pellet (40% protein) g/100 g protein | Dry material after solvent extraction (70% protein) g/100 g protein |
| Alanine | 7.5 | 6.8 |
| Arginine | 7.3 | 7.5 |
| Aspartic acid | 10.6 | 10.6 |
| Cysteine | 1.2 | 1.3 |
| Glutamic acid | 12.9 | 12.6 |
| Glycine | 5.7 | 5.9 |
| Histidine | 1.8 | 1.7 |
| Isoleucine | 4.2 | 4.0 |
| Leucine | 11.0 | 11.1 |
| Lysine | 7.0 | 7.6 |
| Methoinine | 2.3 | 1.7 |
| Phenylalanine | 5.8 | 5.7 |
| Proline | 3.3 | 2.8 |
| Serine | 4.7 | 4.9 |
| Threonine | 5.4 | 5.5 |
| Tryptophane | 0.7 | 0.4 |
| Tyrosine | 3.7 | 3.9 |
| Valine | 5.8 | 5.7 |

In the accompanying drawing, the FIGURE, magnified 4500×, shows *Dunaliella bardawil.*

The characteristics of the algae in accordance with the present invention are summarized on the following table:

Nomenclature data:

*Genus.*—Dunaliella.

*Species.*—*bardawil.*

*Authority.*—Named by Dr. Ami Ben-Amotz and Prof. Mordhay Avron, Department of Biochemistry, Weizmann Institute of Science.

History and origin:

*Isolated from.*—Natural salt pond near Bardawil Lagoon, North Sinai, latitude 31°07′, longitude 33°30′. This salt pond, known as Lake Bardawil, is a cultivated pond, because nutrients are added to this pond.

*Collected and isolated by.*—Dr. A. Ben-Amotz.

*Identified by.*—Dr. A. Ben-Amotz and Prof. M. Avron.

Maintenance:

*Method of preservation.*—Agar culture. May be maintained also in liquid growth medium.

*Temperature of preservation.*—5° to 20° C.

*Preservation suspending medium.*—Liquid growth medium or 1.5–2% agar added to growth medium on plates or slants.

*Growth medium.*—McLachlan, J. 1960, Can. J. Microbiol. 6, 367. Ben-Amotz, A., 1975, J. Phycol. 11, 50, with the addition of 1–4 M NaCl.

*Growth conditions.*—Bubbling 1–2% $CO_2$ in air, or addition of 10 mM $NaHCO_3$ to the growth medium in the presence of 20 mM TRIS, pH 7.5.

Special features and usage:

Anatomical part. Similar to that described by Butcher (Butcher, R. W. 1959, Fish. Invest. Ser. 4,1) for *D. salina* except for size (length 15–19 μm; diameter 10–14 μm; volume 200–1000 $um^3$). Under defined conditions (see below), the alga contains up to 9% of its dry weight as carotene isomers and up to 50% as glycerol.

Favorable conditions for high production of carotene

*Light.*—High light intensity (1500 f.c. up to full sunlight). When grown outdoors in a thin layer (3–10 cm), the cells are bright orange, as a result of massive accumulation of carotene (see table). When grown indoors with artificial illumination (200–400 f.c.), the cells gradually lose most of the orange color and become green. This transition is reversible.

*NaCl.*—High concentration of NaCl (above 3.0 M).

*Nitrogen source.*—Below 1 mM.

*Diurnal cycle.*—With the high light intensities optimal for carotene production, growth is maximal only under a diurnal cycle; such a cycle can be achieved by growth outdoors or by a 14 hours light—10 hours dark cycle indoors. Severe inhibition of growth occurs when the cells are exposed continuously (24 hours daily) to high light intensity.

| Content of β-carotene, Glycerol, Chlorophyll and Protein under favorable conditions: | | |
|---|---|---|
| | Growth outdoors, 3 M NaCl | Growth indoors, 3 M NaCl |
| β-carotene pg/cell | 50–90 | 8–16 |
| Glycerol pg/cell | 300–400 | 200–275 |
| Chlorophyll pg/cell | 4–8 | 10–16 |
| Carotene mg/g dry wt. | 50–90 | 10–21 |
| Glycerol mg/g dry wt. | 300–400 | 270–370 |
| Chlorophyll mg/g dry wt. | 8–12 | 13–21 |

-continued

| Content of β-carotene, Glycerol, Chlorophyll and Protein under favorable conditions: | | |
|---|---|---|
| | Growth outdoors, 3 M NaCl | Growth indoors, 3 M NaCl |
| Protein mg/g dry wt. | 300–400 | 300–400 |

What is claimed is:

1. A new and distinct variety of alga of the genus Dunaliella, named *Dunaliella bardawil,* substantially as herein shown and described, characterized by the fact that when grown outdoors in a thin layer the cells are bright orange, the cells containing up to 9% dry weight of carotene and up to 50% glycerol.

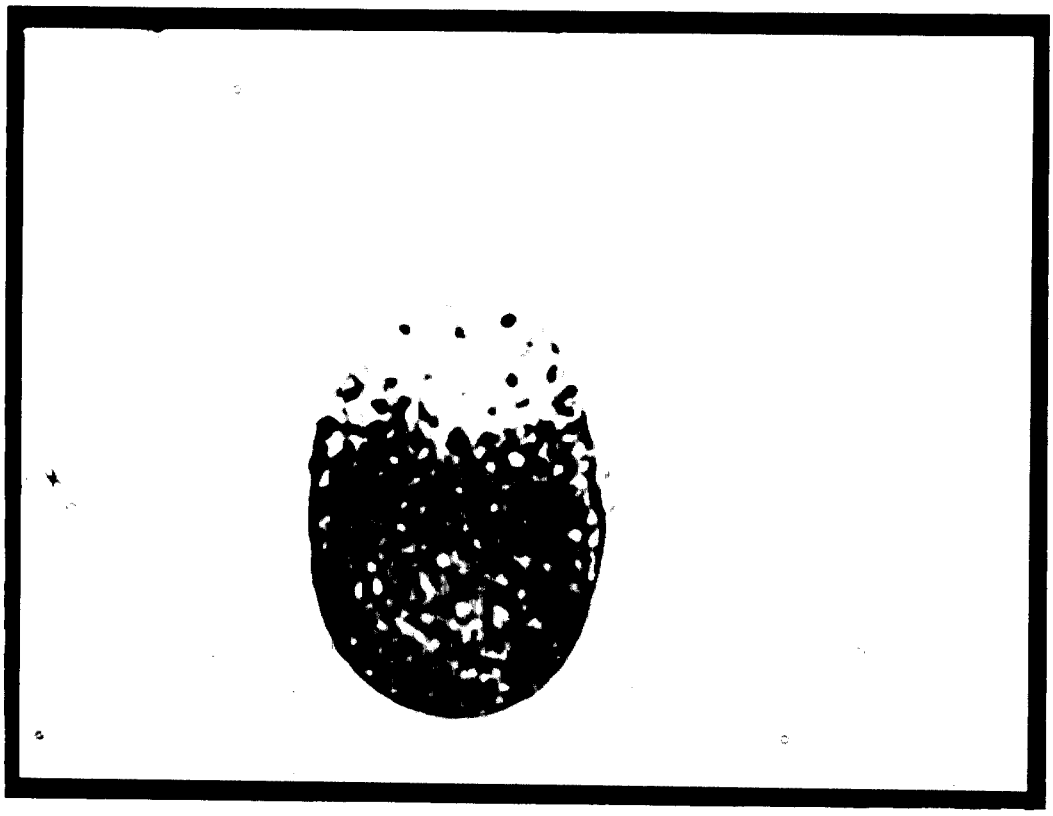

* * * * *